United States Patent [19]

St. Georgiev et al.

[11] Patent Number: 4,727,156
[45] Date of Patent: Feb. 23, 1988

[54] 3-(SUBSTITUTED PHENYL)-3-(1H-IMIDAZOL-1-YLMETHYL)-2-METHYL-5-{[(SUBSTITUTED PHENYL)THIO]METHYL}ISOXAZOLIDINE DERIVATIVES

[75] Inventors: Vassil St. Georgiev, Rochester; George B. Mullen, Avon, both of N.Y.

[73] Assignee: Pennwalt Corporation, Philadelphia, Pa.

[21] Appl. No.: 900,853

[22] Filed: Aug. 27, 1986

[51] Int. Cl.$^4$ ............................................ C07D 233/60
[52] U.S. Cl. ....................................... 548/240; 568/38; 568/56
[58] Field of Search ........................................ 548/240

[56] References Cited

U.S. PATENT DOCUMENTS

| | | | |
|---|---|---|---|
| 3,711,495 | 1/1973 | Kulsa et al. | 548/240 |
| 3,915,978 | 10/1975 | Kulsa et al. | 548/240 |
| 3,987,179 | 10/1976 | Nadelson | 514/378 |

FOREIGN PATENT DOCUMENTS 54-76579  6/1979  Japan .

OTHER PUBLICATIONS

Kelly, R. C. et al., Chemical Abstract 93:114498u (1980), Abstracting German Offen. 2,918,878 (Nov. 22, 1979).
Haken, P. T. et al., Chemical Abstract 93:132471; (1980), Abstracting Brit. Pat. Appln. 2,024,218 (Jan. 9, 1980).
Takahi, Y. et al., Chemical Abstract 81:22233c (1974), Abstracting Japan Kokai 7399,336 (Dec. 15, 1973).
Boyce, C. B. et al., Chemical Abstract 87:23258a (1977), Abstracting German Offen. 2,639,189 (Mar. 10, 1977).
Funaki, Y. et al., Chemical Abstract 92:128915a (1980), Abstracting Japan Kokai 79 76,579 (Jun. 19, 1979).
Sokolov, S. V. et al., Chemical Abstract 55:7399 (1961), "Isoxazale Compounds III. Synthesis of Some Isoxazolylazoles", Abstracting Zhur. Obshshei Khim. 30, pp. 1781-1787 (1960).
Kano, H. et al., Chem. Abstract 62:9139a (1965), Abstracting French 1,376,432 (Oct. 23, 1964).
Kano, H. et al., Chemical Abstract 63:8367a (1965), Abstracting French 1,380,177 (Nov. 27, 1964).

*Primary Examiner*—Donald G. Daus
*Assistant Examiner*—Barbara Cassatt

[57] ABSTRACT

3-(Substituting phenyl)-3-(1H-imidazol-1-ylmethyl)-2-methyl-5-{[(substituted phenyl)thio]methyl}isoxazolidines in which hydrogens of their phenyl rings may be replaced by halogen, lower alkoxy, lower alkyl or nitro groups, and the sulfur atom may be oxidized, are useful as antifungal agents.

16 Claims, No Drawings

3-(SUBSTITUTED PHENYL)-3-(1H-IMIDAZOL-1-YLMETHYL)-2-METHYL-5-{[(SUBSTITUTED PHENYL)THIO]METHYL}ISOXAZOLIDINE DERIVATIVES

BACKGROUND OF THE INVENTION

This invention relates generally to substituted 3-(substituted phenyl)-3-(1H-imidazol-1-ylmethyl)-2-methyl-5-{[(substituted phenyl)thio ]methyl}isoxazolidine derivatives which are useful as antifungal agents.

BRIEF SUMMARY OF THE INVENTION

In accordance with this invention there are provided compounds of the formula:

and pharmaceutically acceptable acid addition salts thereof, in the form of their enantiomers, or mixtures of their enantiomers including diasteroisomeric pairs of such enantiomers, wherein;
a=1 or 2,
b=1 or 2,
$R^1$ is selected from hydrogen, halogen, lower alkoxy, lower alkyl, and combinations thereof, provided the ortho position is hydrogen, and
$R^2$ is selected from hydrogen, halogen, lower alkyl, lower alkoxy, nitro, and combinations thereof, and
n=0 to 2.

DETAILED DESCRIPTION OF THE INVENTION

The compound of this invention are useful as antifungal agents. They have been shown to possess activity against yeast and systemic mycoses and dermatophytes in in vitro experiments as determined by broth and agar testing techniques [McGinnis, M. R., *Laboratory Handbook of Medical Mycology*, Academic Press, N.Y., N.Y., (1980)]. The compounds prepared in Examples 4 to 7, 10 and 11 were tested and found to have inhibitory activity against a broad spectrum of organisms including trichopyton mentagrophytes, trichopyton tonsurans, trichopyton schoenleinii, epidermopyton floccosum, trichophyton rubrum, microsporum canis, candida albicans and candida stellatoidea (minimum inhibitory concentrations, MIC, of <0.2 to 7 ug/ml).

Because of the antifungal activity of the compounds of the invention they can be used, for example, in suitable liquid, semi-solid or solid carriers in the form of solutions, emulsions, suspensions, dispersions, ointments, aerosols, soaps, detergents, and powders in amounts effective to combat systemic and dermatophylic fungal infections in warm blooded animals (1 to 20 percent active ingredient).

The compounds of this invention are those of the formula:

and pharmaceutically acceptable acid addition salts thereof, in the form of their enantiomers, or mixtures of their enantiomers including diastereoisomeric pairs of such enantiomers, wherein;
a=1 or 2,
b=1 or 2,
$R^1$ is selected from hydrogen, halogen, lower alkoxy, lower alkyl, and combinations thereof, provided the ortho position is hydrogen, and
$R^2$ is selected from hydrogen, lower alkyl, lower alkoxy, halogen, nitro, and combinations thereof.

The sulfur atom may be oxidized to provide the corresponding sulfoxide and sulfone analogs (n=1 or 2, respectively). By halogen is meant chlorine, bromine, fluorine and iodine with chlorine and fluorine being preferred. By lower alkyl and lower alkoxy is meant $C_1$ to $C_4$ which may be a branched or unbranched chain. Compounds having ortho substitution of the upper phenyl group were not prepared probably due to steric hindrance.

The 3-(substituted phenyl)-3-(1H-imidazol-1-ylmethyl)-2-methyl -5-{[(substituted phenyl)thio]methyl}isoxazolidine derivatives are obtained as mixtures of the corresponding cis- and trans-diastereomers due to the presence of two asymmetric carbon atoms in the isoxazolidine ring. The diastereomeric mixture is conveniently separated by flash-chromatography on silica gel using solvents such as halogenated hydrocarbons (preferably dichloromethane and chloroform), alkanols (preferably methanol and ethanol), and ethyl acetate as eluents. The eluents may be used alone or in combinations such as the ones comprised of 95-99% halogenated hydrocarbon and 1-5% alkanol by volume. The stereochemistry of the two asymmetric carbon atoms in the isoxazolidine ring may be determined by conventional methods that include x-ray crystallography, nuclear magnetic resonance spectroscopy, circular dichroism or optical rotatory dispersion. Both the cis and trans stereoisomers are resolvable into their optical enantiomers with (+) and (−) optical rotations by standard techniques such as fractional recrystallization of the diastereomeric salts with optically active organic acids such as (+) and (−) tartaric acid, (+) and (−) dibenzoyltartaric acid and the like.

The compounds can be prepared as illustrated in the following diagram. The synthesis of the nitrone precursors 1 is accomplished by reacting an appropriately substituted imidazolylacetophenone compound with N-methylhydroxylamine hydrochloride as disclosed in a co-pending application filed concurrently herewith and commonly assigned entitled "α-Substituted Ketonitrone Derivatives" whose disclosure is incorporated herein by reference. Then, the nitrone derivative 1 is treated with an appropriate allyl (substituted phenyl) sulfide (compound 2) to provide a diastereomeric mixture of the desired cis- and trans-3 (substituted phenyl)-3-(1H-imidazol-1-yl) methyl-2-methyl -5-{[(substituted phenyl)thio]methyl}isoxazolidine derivative 3.

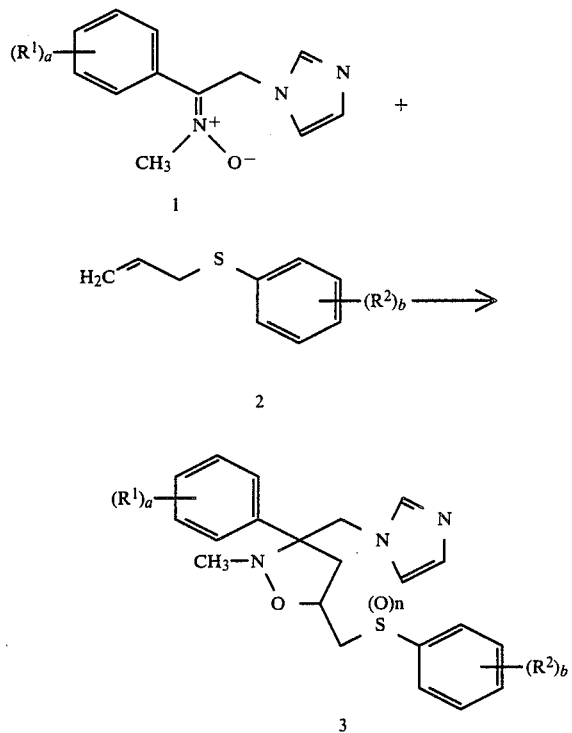

The compounds of the invention are all basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation of the compounds of the invention is further illustrated by the following synthesis of the allyl (substituted)phenyl sulfide intermediates and in the Examples.

PREPARATION OF ALLYL (SUBSTITUTED)PHENYL SULFIDES (2)

The allyl (substituted)phenyl sulfides 2 can be prepared by the method of Hurd and Greengard, *J. Am. Chem. Soc.*, 52, 3356–3358 (1930).

The following allyl (substituted)phenyl sulfides 2 were synthesized.
(a) allyl phenyl sulfide, bp 65° C. (0.75 mm),
(b) allyl 4-chlorophenyl sulfide, bp 90° C. (0.15 mm),
(c) allyl 4-methylphenyl sulfide, bp 50°–53° C. (0.15 mm),
(d) allyl 4-nitrophenyl sulfide, bp 95° C. (0.09 mm),
(e) allyl 4-fluorophenyl sulfide, bp 52°–54° C. (0.15 mm), and
(f) allyl 2-methoxyphenyl sulfide bp 77°–80° C. (0.50 mm).

EXAMPLE 1

3-(3-Methoxyphenyl)-3-(1H-imidazol-1-ylmethyl)-2-methyl-5-{[(4-chlorophenyl)thio]methyl}isoxazolidine (3, $R^1$=3-CH$_3$O, $R^2$=4-Cl, n=0)

A solution of 29.4 g (0.12 mol) of 2-(1H-imidazol-1-yl)-1-(3-methoxyphenyl)-N-methylethanimine N-oxide (1, $R^1$=3—OCH$_3$) [prepared by reacting 2-(1H-imidazol-1-yl)-3'-methoxyacetophenone (24.03g 0.120 mol) with N-methylhydroxylamine hydrochloride (12.05 g 0.144 mol) and sodium bicarbonate (12.10 g 0.144 mol) in 300 ml of ethanol] and 29.5 g (0.16 mol) of allyl 4-chlorophenyl sulfide (2, $R^2$=4—Cl) in 300 ml of toluene was refluxed for 24 hours under a nitrogen atmosphere.

Then, the reaction mixture was cooled to room temperature and the solvent evaporated under reduced pressure. The crude cis- and trans-diastereomeric mixture of the title compound was flash-chromatographed on neutral silica gel using ethyl acetate as the eluent.

Isomer A (5.69 g) has a melting point of 113°–114° C. (ethyl acetate).

Anal. Calcd for $C_{22}H_{24}ClN_3O_2S$: C, 61.46; H 5.63; N, 9.77; Cl, 8.25; S, 7.46. Found: C, 61.35; H, 5.65; N, 9.71; Cl, 8.59; S, 7.57.

EXAMPLE 2

3-(4-Chlorophenyl)-3-(1H-imidazol-1-ylmethyl)-2-methyl -5-[(phenylthio)methyl]isoxazolidine (3, $R^1$=4—Cl, $R^2$=H, n=0)

The title compound was prepared by a procedure similar to that described in Example 1 by reacting 1-(4-chlorophenyl)-2-(1H-imidazol-1-yl)-N-methylethanimine N-oxide (1, $R^1$=4—Cl) with allyl phenyl sulfide (2, $R^2$=H). The resulting cis- and trans-diastereomeric mixture of the title compound was flash-chromatographed on neutral silica gel using ethyl acetate as eluent.

Isomer A has a melting point of 81°–88° C. (ethyl acetate-petroleum ether, 1:1 by volume).

Anal. Calcd. for $C_{21}H_{22}ClN_3OS$: C, 63.07; H, 5.54; N, 10.51; CL, 8.86. Found: C, 62.98; H, 5.62; N, 10.44; Cl, 9.15. Isomer B has a melting point of 81°–85° C. (ether).

EXAMPLE 3

3-(3-Methoxyphenyl)-3-(1H-imidazol-1-ylmethyl)-2-methyl-5-{[(4-methylphenyl)thio]methyl}isoxazolidine (3, $R^1$=3—OCH$_3$, $R^2$=4—CH$_3$, n=0)

The title compound was prepared by a procedure similar to that described in Example 1 by reacting 2-(1H-imidazol-1-yl)-1-(3-methoxyphenyl)-N-methylethanimine N-oxide (1, $R^1$=3—OCH$_3$) with allyl 4-methyphenyl sulfide (2: $R^2$=4—CH$_3$). The resulting cis- and trans-diastereomeric mixture of compound 3 ($R^1$=3—OCH$_3$, $R^2$=4—CH$_3$, n=0) was flash-chromatographed on neutral silica gel using ethyl acetate as eluent.

Isomer A has a melting point of 107°–108° C. (ethyl acetate).

Anal. Calcd. for $C_{23}H_{27}N_3O_2S$: C, 67.45; H, 6.65; N, 10.26; S, 7.83. Found: C, 67.37; H, 6.59: N, 10.22; S, 8.02.

EXAMPLE 4

3-(4-Chlorophenyl)-3-(1H-imidazol-1-ylmethyl)-2-methyl-5-{[(4-methylphenyl)thio]methyl}isoxazolidine (3: $R^1=4-Cl$, $R^2=4-CH_3$, n=0)

Compound 3 ($R^1=4-Cl$, $R^2=4-CH_3$, n=0) was prepared by a procedure similar to that described in Example 1 by reacting 1-(4-chlorophenyl)-2-(1H-imidazol-1-yl)-N-methylethanimine N-oxide (1, $R^1=4-Cl$) with allyl 4-methylphenyl sulfide (2, $R^2=4-CH_3$). The resulting cis- and trans-diastereomeric mixture of the title compound was flash-chromatographed on neutral silica gel using ethyl acetate as eluent.

Isomer A has a melting point of 98°–100° C. (ethyl acetate).

Anal. Calcd for $C_{22}H_{24}ClN_3OS$: C, 64.00; H, 5.84; N, 10.15; Cl, 8.56; S, 7.75. Found: C, 63.98; H, 5.98; N, 10.11; Cl, 8.68; S, 7.84.

The preparation was repeated except that nitrone 1 was prepared using sodium acetate in place of sodium bicarbonate.

EXAMPLE 5

3-(4-Chlorophenyl)-3-(1H-imidazol-1-ylmethyl)-2-methyl-5-{[(4-fluorophenyl)thio]methyl}isoxazolidine (3, $R^1=4-Cl$, $R^2=4-F$, n=0)

Compound 3 ($R^1=4-Cl$, $R^2=4-F$, n=0) was prepared by a procedure similar to that described in Example 1 by reacting 1-(4-chlorophenyl)-2-(1H-imidazol-1-yl)-N-methylethanimine N-oxide (1, $R^1=4-Cl$) with allyl 4-fluorophenyl sulfide (2, $R^2=4-F$). The resulting cis- and trans-diastereomeric mixture of the title derivative was flash-chromatographed on neutral silica gel using ethyl acetate as eluent.

Isomer A has a melting point of 106°–107° C. (ethyl acetate-hexane, 1:1 by volume).

Anal. Calcd for $C_{21}H_{21}ClFN_3OS$: C, 60.35; H, 5.06; N, 10.05; Cl, 8.48; F, 4.55; S, 7.67. Found: C, 60.08; H, 4.84; N, 9.99; Cl, 8.57; F, 4.61; S, 8.02.

EXAMPLE 6

3-(4-Chlorophenyl)-3-(1H-imidazol-1-ylmethyl)-2-methyl-5-{[(4-nitrophenyl)thio]methyl}isoxazolidine (3, $R^1=4-Cl$, $R^2=4-NO_2$, n=0)

Compound 3 ($R^1=4-Cl$, $R^2=4-NO_2$, n=0) was prepared by a procedure similar to that described in Example 1 by reacting 1-(4-chlorophenyl)-2-(1H-imidazol-1-yl)-N-methylethanimine N-oxide (1, $R^1=4-Cl$) with allyl 4-nitrophenyl sulfide (2, $R^2=4-NO_2$). The resulting cis- and trans-diastereomeric mixture of the title compound was flash-chromatographed on neutral silica gel using a 98:2 by volume mixture of chloroform and methanol as eluent.

Isomer A has a melting point of 179°–180° C. (ethanol).

Anal. Calcd for $C_{21}H_{21}ClN_4O_3S$: C, 56.69; H, 4.76; N, 12.59; Cl, 7.97; S, 7.21. Found: C, 56.47; H, 4.90; N, 12.39; Cl, 8.21; S, 7.46.

EXAMPLE 7

3-(4-Chlorophenyl)-3-(1H-imidazol-1-ylmethyl)-2-methyl-5-{[(4-chlorophenyl)thio]methyl}isoxazolidine (3, $R^1=R^2=4-Cl$, n=0)

Compound 3 ($R^1=R^2=4-Cl$, n=0) was prepared according to a procedure similar to that described in Example 1 by reacting 1-(4-chlorophenyl)-2-(1H-imidazol-1-yl)-N-methylethanimine N-oxide (1, $R^1=4-Cl$) with allyl 4-chlorophenyl sulfide (2, $R^2=4-Cl$). The resulting cis- and trans-diastereomeric mixture of compound 3 ($R^1=R^2=4-Cl$, n=0) was flash-chromatographed on neutral silica gel using a 99:1 by volume mixture of chloroform and methanol as eluent.

Isomer A has a melting point 118°–119° C. (ethyl acetate).

Anal. Calcd for $C_{21}H_{21}Cl_2N_3OS$: C, 58.07; H, 4.87; N, 9.67; Cl, 16.32; S, 7.38. Found: C, 58.12; H, 4.95; N, 9.67; Cl, 16.29; S, 7.64.

EXAMPLE 8

3-Phenyl-3-(1H-imidazol-1-ylmethyl)-2-methyl-5-{[(4-chlorophenyl)thio]methyl}isoxazolidine (3, $R^1=H$, $R^2=4-Cl$, n=0)

Compound 3 ($R^1=H$, $R^2=4-Cl$, n=0) was prepared by a procedure similar to that described in Example 1 by reacting 1-phenyl-2-(1H-imidazol-1-yl)-N-methylethanimine N-oxide (1, $R^1=H$) with allyl 4-chlorophenyl sulfide (2, $R^2=4-Cl$). The resulting cis- and trans-diastereomeric mixture of the title derivative was flash-chromatographed on neutral silica gel using chloroform-methanol (98:2 by volume) as eluent.

Isomer A has a melting point of 132.5°–133° C. (ethyl acetate).

Anal. Calcd for $C_{21}H_{22}ClN_3OS$: C, 63.07, H, 5.54; N, 10.51; Cl, 8.86; S, 8.02. Found: C, 62.93; H, 5.55; N, 10.45; Cl, 9.32; S, 8.50.

EXAMPLE 9

3-Phenyl-3-(1H-imidazol-1-ylmethyl)-2-methyl-5-{[(4-methyl-phenyl)thio]methyl}isoxazolidine (3, $R^1=H$, $R^2=4-CH^3$, n=0)

Compound 3 ($R^1=H$, $R^2=4-CH_3$, n=0) was prepared according to a procedure similar to that described in Example 1 by reacting 1-phenyl-2-(1H-imidazol-1-yl)-N-methylethanimine N-oxide (1, $R^1=H$) with allyl 4-methylphenyl sulfide (2, $R^2=4-CH_3$). The resulting cis- and trans-diastereomeric mixture of the title compound was flash-chromatographed on neutral silica gel using chloroform-methanol (98:2 by volume) as eluent.

Isomer A has a melting point of 116° C. (ethyl acetate).

Anal. Calcd for $C_{22}H_{25}N_3OS$: C, 69.63; H, 6.64; N, 11.07; S, 8.45. Found: C, 69.53; H, 6.69; N, 11.01; S, 8.54.

EXAMPLE 10

3-(4-Fluorophenyl)-3-(1H-imidazol-2-ylmethyl)-2-methyl-5-{[(4-chlorophenyl)thio]methyl}isoxazolidine (3, $R^1=4-F$, $R^2=4-Cl$, n=0)

Compound 3 ($R^1=4-F$, $R^2=4-Cl$, n=0) was prepared by a procedure similar to that described in Example 1 by reacting 1-(4-fluorophenyl)-2-(1H-imidazol-1-yl)-N-methylethanimine N-oxide (1, $R^1=4-F$) with allyl 4-chlorophenyl sulfide (2, $R^2=4-Cl$). The resulting cis- and trans-diastereomeric mixture of compound 3 ($R^1=4-F$, $R^2=4-Cl$, n=0) was flash-chromatographed on neutral silicia gel using ethyl acetate as eluent.

Isomer A has a melting point of 12.5° C. (ethyl acetate).

Anal. Calcd for $C_{21}H_{21}ClFN_3OS$: C, 60.35; H, 5.06; N, 10.05; Cl, 8.84; F, 4.55; S, 7.67. Found: C, 60.30; H, 5.12; N, 10.04; Cl, 8.48; F, 4.43; S, 7.88, The above preparation was repeated except that nitrone 1 was prepared using sodium acetate in place of sodium bicarbonate.

EXAMPLE 11

3-(4-Fluorophenyl)-3-(1H-imidazol-1-ylmethyl)-2-methyl-5-{[(4-methylphenyl)thio]methyl}isoxazolidine (3, $R^1=4$—F, $R^2=4$—$CH_3$, n=0)

Compound 3 ($R^1=4$—F, $R^2=4$—$CH_3$, n=0) was prepared by a procedure similar to that described in Example 1 by reacting 1-(4-fluorophenyl)-2-(1H-imidazol-1-yl)-N-methyle-thanimine N-oxide (1, $R^1=4$—F) with allyl 4-methylphenyl sulfide (2, $R^2=4$—$CH_3$). The resulting cis- and trans-diastereomeric mixture of compound 3 ($R^1=4$—F $R^2=4$—$CH_3$, n=0) was flash-chromatographed on neutral silica gel using a 99:1 by volume mixture of chloroform and methanol as eluent.

Isomer A has a melting point of 109.5°–110° C. (ethyl acetate).

Anal. Calcd for $C_{22}H_{24}FN_3OS$: C, 66.47; H, 6.09; N, 10.57; F, 4.78; S, 8.07. Found: C, 66.39; H, 6.10; N, 10.69; F, 5.02; S, 8.24.

EXAMPLE 12

3-(3,4-Dichlorophenyl)-3-(1H-imidazol-1-ylmethyl)-2-methyl-5-{[(2-methoxyphenyl)thio]methyl}isoxazolidine (3, $R^1=3,4$—$Cl_2$, $R^2=2$—$OCH_3$, n=0)

Compound 3 ($R^1=3,4$—$Cl_2$, $R^2=2$—$OCH_3$, n=0) was prepared according to a procedure similar to that described in Example 1 by reacting 1-(3,4-dichlorophenyl)-2-(1H-imidazol-1-yl)-N-methylethanimine N-oxide (1, $R^1=3,4$—$Cl_2$) with allyl 2-methoxyphenyl sulfide (2, $R^2=2$—$OCH_3$). The resulting cis-and trans-diastereomeric mixture of compound 3 ($R^1=3,4$-$Cl_2$, $R^2=2$—$OCH_3$, n=0) was flash-chromatographed on neutral silica gel using ethyl acetate as eluent.

Isomer A has a melting point of 55°–65° C. (decomp.) (ethyl acetate).

Anal. Calcd for $C_{22}N_{23}Cl_2N_3O_2S$: C, 56.90; H, 4.99; N, 9.05; Cl, 15.27; S, 6.90. Found: C, 56.53; H, 5.20; N, 8.89; Cl, 15.10; S, 7.08.

EXAMPLE 13

3-(3-Methoxyphenyl)-3-(1H-imidazol-1-ylmethyl)-2-methyl-5-{[(4-chlorophenyl)sulfoxyl]methyl}isoxazolidine (3, $R^1=OCH_3$, $R^2=4$—Cl, n=1)

Under a nitrogen atmosphere, a solution of 2.0 g (4.65 mmol) of 3-(3-methoxyphenyl)-3-(1H-imidazol-1-ylmethyl)-2-methyl-5-{[(4-chlorophenyl)thio]methyl}isoxazolidine (3, $R^1=3$—$OCH_3$, $R^2=4$—Cl, n=0, isomer A) in 100 ml of methylene chloride was cooled to −78° C. using a dry ice-acetone bath. To this solution was added dropwise over a period of 30 minutes, a solution of 1.24 g (5.75 mmol) of 85% m-chloroperbenzoic acid in 70 ml of methylene chloride.

The resulting solution was warmed gradually to room temperature then washed repeatedly with saturated aqueous sodium bicarbonate solution (3×100 ml) and dried over anhydrous magnesium sulfate. The solvent was evaporated under reduced pressure and the crude product was flash-chromatographed on neutral silica gel using a 98:2 by volume mixture of chloroform and methanol as eluent.

A pure compound 3 ($R^1=3$—$OCH_3$, $R^2=4$—Cl, n=1) 0.43 g, 21% yield) was obtained as white crystals Mp 120°–121° C. (ethyl acetate).

Anal. Calcd for $C_{22}H_{24}ClN_3O_3S$: C, 59.25; H, 5.42; N, 9.42; S, 7.19. Found: C, 58.96; H, 5.52; N, 9.32; S, 7.41.

EXAMPLE 14

3-(4-Chlorophenyl)-3-(1H-imidazol-1-ylmethyl)-2-methyl-5-{[(4-chlorophenyl)sulfoxyl]methyl}isoxazolidine (3, $R^1=R^2=4$—Cl, n=1)

Compound 3 ($R^1=R^2=4$—Cl, n=1) was prepared by a procedure similar to that described in Example 13 by reacting 3-(4-chlorophenyl)-3-(1H-imidazol-1-ylmethyl)-2-methyl-5-{[(4-chlorophenyl)thio]methyl}isoxazolidine (3, $R^1=R^2=4$—Cl, n=0, isomer A) with 85% m-chloroperbenzoic acid. The resulting crude compound 3 ($R^1=R^2=4$—Cl, n=1) was flash-chromatographed on neutral silica gel using chloroform-methanol (98:2 by volume) as eluent. Mp 184° C. (ethyl acetate).

Salts of the compounds of the invention can be prepared as known in the art, for example, by dissolving the compound in a 10:1 by volume mixture of ethanol and aqueous acid, evaporating the solvent, and then recrystallizing the crude salt, for example, from methanol-ether, 1:3 by volume in the case of HCl salts, and ethanol in the case of $HNO_3$ salts.

We claim:

1. A compound of the formula:

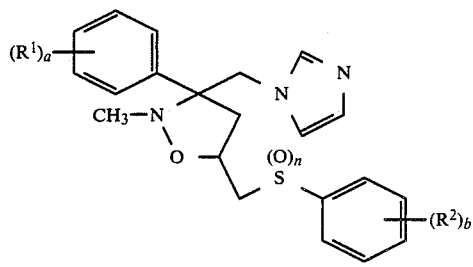

or a pharmaceutically acceptable acid addition salt thereof, in the form of their enantiomers, or mixtures of their enantiomers including diastereoisomeric pairs of such enantiomers, wherein;

a=1 or 2,
b=1 or 2,
$R^1$ is selected from hydrogen, halogen, lower alkyl, lower alkoxy, and combinations thereof, provided that the ortho position is hydrogen,
$R^2$ is selected from hydrogen, halogen, lower alkyl, lower alkoxy, nitro, and combinations thereof, and n=0 to 2.

2. The compound of claim 1 wherein the compound is 3-(3-methoxyphenyl)-3-(1H-imidazol-1-ylmethyl)-2-methyl-5-{[(4-chlorophenyl)thio]methyl}isoxazolidine.

3. The compound of claim 1 wherein the compound is 3-(4-chlorophenyl)-3-(1H-imidazol-1-ylmethyl)-2-methyl-5-[(phenylthio)methyl]isoxazolidine.

4. The compound of claim 1 wherein the compound is 3-(3-methoxyphenyl)-3-(1H-imidazol-1-ylmethyl)-2- methyl-5-{[(4-methylphenyl)thio]methyl}isoxazolidine.

5. The compound of claim 1 wherein the compound is 3-(4-chlorophenyl)-3-(1H-imidazol-1-ylmethyl)-2-methyl-5-{[(4-methylphenyl)thio]methyl}isoxazolidine.

6. The compound of claim 1 wherein the compound is 3-(4-chlorophenyl)-3-(1H-imidazol-1-ylmethyl)-2-methyl-5-{[(4-fluorophenyl)thio]methyl}isoxazolidine.

7. The compound of claim 1 wherein the compound is 3-(4-chlorophenyl)-3-(1H-imidazol-1-ylmethyl)-2-methyl-5-{[(4-nitrophenyl)thio]methyl}isoxazolidine.

8. The compound of claim 1 wherein the compound is 3-(4-chlorophenyl)-3-(1H-imidazol-1-ylmethyl)-2-methyl-5-{[(4-chlorophenyl)thio]methyl}isoxazolidine.

9. The compound of claim 1 wherein the compound is 3-phenyl-3-(1H-imidazol-1-ylmethyl)-2-methyl-5-{[(4-chlorophenyl) thio]methyl}isoxazolidine.

10. The compound of claim 1 wherein the compound is 3-phenyl-3-(1H-imidazol-1-ylmethyl)-2-methyl-5-{[(4-methylphenyl) thio]methyl}isoxazolidine.

11. The compound of claim 1 wherein the compound is 3-(4-fluorophenyl)-3-(1H-imidazol-1-ylmethyl)-2-methyl-5-{[(4-chlorophenyl)thio]methyl}isoxazolidine.

12. The compound of claim 1 wherein the compound is 3-(4-fluorophenyl)-3-(1H-imidazol-1-ylmethyl)-2-methyl-5-{[(4-methylphenyl)thio]methyl}isoxazolidine.

13. The compound of claim 1 wherein the compound is 3-(3,4-dichlorophenyl)-3-(1H-imidazol-1-ylmethyl)-2-methyl -5-{[(2-methoxyphenyl)thio]methyl}isoxazolidine.

14. The compound of claim 1 wherein the compound is 3-(3-methoxyphenyl)-3-(1H-imidazol-1-ylmethyl)-2-methyl-5-{[(4-chlorophenyl)sulfoxyl]methyl}isoxazolidine.

15. The compound of claim 1 wherein the compound is 3-(4-chlorophenyl)-3-(1H-imidazol-1-ylmethyl)-2-methyl-5-{[(4-chlorophenyl)sulfoxyl]methyl}isoxazolidine.

16. The compound of claim 1 wherein the compound is a diastereoisomeric pair of enantiomers.

* * * * *